(12) United States Patent
Xiu

(10) Patent No.: US 7,074,440 B2
(45) Date of Patent: Jul. 11, 2006

(54) COMPOSITIONS AND METHODS FOR BODY WEIGHT LOSS

(76) Inventor: Rulin Xiu, 2702 13th St., NW., Washington, DC (US) 20009

( * ) Notice: Subject to any disclaimer, the term of this patent is extended or adjusted under 35 U.S.C. 154(b) by 19 days.

(21) Appl. No.: 10/373,659

(22) Filed: Feb. 26, 2003

(65) Prior Publication Data

US 2004/0001862 A1    Jan. 1, 2004

Related U.S. Application Data

(60) Provisional application No. 60/376,526, filed on May 1, 2002.

(51) Int. Cl.
*A61K 35/78* (2006.01)

(52) U.S. Cl. .................. 424/728; 424/195.1; 424/729; 424/725

(58) Field of Classification Search ............. 424/195.1, 424/725, 729, 728, 773, 195.17
See application file for complete search history.

(56) References Cited

U.S. PATENT DOCUMENTS 6,365,176 B1 *   4/2002   Bell et al. ................... 424/439
2002/0136785 A1 *   9/2002   Yuan .......................... 424/728

FOREIGN PATENT DOCUMENTS

CN       1126091 A    *   7/1996

OTHER PUBLICATIONS

Dulloo et al. : Efficacy of a Green Tea Extract Rich in Catechin Polyphenols and Caffeine in Increasing 24-H Energy Expenditure and Fat Oxidation in Humans; Am. J. Clin Nutr. (1999); 70: pp. 1040-1045.*

* cited by examiner

*Primary Examiner*—Patricia Leith
(74) *Attorney, Agent, or Firm*—Millen, White, Zelano & Branigan, P.C.

(57) ABSTRACT

The present invention relates to herbal compositions and methods for regulating body weight, especially for promoting body weight loss, for maintaining or controlling body weight, reducing blood levels of circulating chemical fuels (e.g., glucose, carbohydrates, fatty acids, and cholesterol), facilitating or promoting metabolism, treating diabetes, treating body weight disorders, and the like.

16 Claims, No Drawings

COMPOSITIONS AND METHODS FOR BODY WEIGHT LOSS

The present application claims the benefit of U.S. Provisional Application Ser. No. 60/376,526, filed May 1, 2002, which is hereby incorporation by reference in its entirety.

DESCRIPTION OF THE INVENTION

The present invention relates to herbal compositions and methods for regulating body weight, especially for promoting body weight loss, for maintaining or controlling body weight, reducing blood levels of circulating chemical fuels (e.g., glucose, carbohydrates, fatty acids, and cholesterol), facilitating or promoting metabolism, treating diabetes, treating body weight disorders, and the like.

Compositions useful for modulating weight loss, include:

1. An herbal composition comprising at least two ingredients selected from rhubarb, green tea, or chitosan, wherein each ingredients is an amount effective to promote body weight loss, maintain or control body weight, reduce blood levels of circulating chemical fuels, facilitate or promote metabolism, treat diabetes or other blood sugar disorders, etc. A composition can comprise, e.g., all three ingredients, or pairs of ingredients, such as rhubarb and green tea, rhubarb and chitosan, and green tea and chitosan 2. An herbal composition comprising rhubarb, green tea, and/or sea weed, wherein each is present in an amount effective to promote body weight loss, maintain or control body weight, reduce blood levels of circulating chemical fuels, facilitate or promote metabolism, treat diabetes or other blood sugar disorders, etc. A composition can comprise, e.g., all three ingredients, or pairs of ingredients, such as rhubarb and sea weed and green tea and sea weed.

3. An herbal composition comprising rhubarb, green tea, and konjac, wherein each is present in an amount effective to promote body weight loss, maintain or control body weight, reduce blood levels of circulating chemical fuels, facilitate or promote metabolism, treat diabetes or other blood sugar disorders, etc. A composition can comprise, e.g., all three ingredients, or pairs of ingredients as long as konjac is included, e.g., rhubarb and konjac, or green tea and konjac.

4. Herbal compositions of formula 1,2, and 3 can further comprise one or more additional ingredients selected from: green tea, konjac, sea weed, ginger root, hawthorn fruit, lotus leaf, alisma root, duckmeat herb, wolfberry fruit, jujube fruit, sparganium root, and rice vinegar, wherein each is present in an amount effective to promote body weight loss, maintain or control body weight, reduce blood levels of circulating chemical fuels, facilitate or promote metabolism, treat diabetes or other blood sugar disorders, etc.

5. An herbal composition comprising rhubarb root, lotus leaf, duckmeat herb, cinnamomi stem, bitter orange, and alisma, wherein each is present in an amount effective to promote body weight loss, maintain or control body weight, reduce blood levels of circulating chemical fuels, facilitate or promote metabolism, treat diabetes or other blood sugar disorders, etc.

6. Herbal compositions of formula 5, can further comprise one or more additional ingredients selected from: hawthorn fruit, red rooted sage, areca catechu fruit, and perilla fruit, wherein each is present in an amount effective to promote body weight loss, maintain or control body weight, reduce blood levels of circulating chemical fuels, facilitate or promote metabolism, treat diabetes or other blood sugar disorders, etc. 7. An herbal composition comprising one or more of the following ingredients: green tea, ginseng, konjac and seaweed, wherein each is present in an amount effective to promote body weight loss, maintain or control body weight, reduce blood levels of circulating chemical fuels, facilitate or promote metabolism, treat diabetes or other blood sugar disorders, etc. The composition can further comprise one or more of any of the other ingredients mentioned herein.

Various combinations of the ingredients can be used, including, e.g.,

According to formula 1, (1) An herbal composition, comprising green tea from about 25–70% by weight of said composition, rhubarb root from about 25–80% by weight of said composition, and chitosan from about 1–75% by weight of said composition. Any amount of ingredients can be used which are effective to achieve the desired purpose. For instance, about 0.5 gram–20 gms, 0.5–5 gms, 0.5–3 gms, 2 gms, can be administered one or more times a day, such as three times a day, depending upon the subject's physical condition and the potency of the ingredients included.

(2) An herbal composition comprising: green tea extract, from about 40–60%, such as 45%, e.g., 500 mg; rhubarb 5:1 extract, from about 40–50%, such as 45%, e.g., 450 mg; and chitosan containing 90% Deacetylation, from about 5–15%, such as 5%, e.g., 50 mg.

(3) An herbal composition comprising: green tea extract, from about 40–60%, such as 50%, e.g., 500 mg; and rhubarb root 5:1 extract, from about 40–50%, such as 50%, e.g., 500 mg.

(4) An herbal composition comprising: rhubarb root 5:1 extract, from about 25–40%, such as 25%, e.g., 500 mg; and chitosan containing 90% Deacetylation, from about 55–75%, such as 75%, e.g., 1500 mg.

(5) An herbal composition comprising: green tea extract, from about 25–35%, such as 25%, e.g., 500 mg; rhubarb root 5:1 extract, from about 25–35%, such as 25%, e.g., 500 mg; and chitosan containing 90% Deacetylation from about 34–60%, such as 50%, e.g., 1000 mg.

(6) An herbal composition comprising green tea extract from about 25–70%, rhubarb root 5:1 extract from about 25–50%, hawthorn fruit 5:1 extract from about 5–30%, lotus leaf 5:1 extract from about 4–20%, alisma root 5:1 extract from about 5–30%, and duckmeat leaf 5:1 extract from about 4–20%. An example of such formula is green tea leaf 5:1 extract from about 30%, rhubarb root 5:1 extract from about 40%, hawthorn fruit 5:1 extract from about 10%, lotus leaf 5:1 extract from about 6%, and alisma root 5:1 extract from about 8%, and duckmeat leaf 5:1 extract from about 6%.

According to formula 2, (1) An herbal composition, comprising green tea leaf extract comprising from about 25–70% by weight of said composition, rhubarb root from about 25–50% by weight of said composition, and sea weed from about 5–75% by weight of said composition. Examples include, where the green tea extract is present in about 30%, the rhubarb root 5:1 extract in about 50%, and sea weed dry powder in 20%; where the green tea extract is present in about 45%, the rhubarb 5:1 extract in about 40% and the sea weed dry powder in 15%. Any effective amount of the composition can be administered. For instance, about 0.5 gram–20 gms, 0.5–5 gms, 0.5–3 gms, 2 gms, can be administered one or more times a day, such as three times a day, depending upon the subject's physical condition and the potency of the ingredients included.

(2) The composition of (1) can further comprise sparganium from about 5–30% and ginseng root from about 3–15%. Examples include, where the green tea extract is present in about 35%, the rhubarb root 5:1 extract in about 45%, sea weed dry powder in about 10%, sparganium 5:1 extract in about 15%, and ginseng root powder in about 3%; where the green tea extract is present in about 50%, the rhubarb 5:1 extract in about 15%, sea weed dry powder in about 20%; sparganium 5:1 extract in about 10%; and ginseng root powder in about 5%.

(3) The composition of (1) can further comprise rice vinegar from about 30–300 liters per 100 kilograms of said composition. Examples include, where the green tea extract is present in about 30%, rhubarb root 5:1 extract in about 50%, sea weed dry powder in about 3%, hawthorn fruit 5:1 extract in about 10%, wolfberry fruit 5:1 extract in about 6%, and jujube fruit 5:1 extract in about 1%, and 50 liter rice vinegar for every 20 kilograms of the above composition.

According to formula 3, (1) An herbal composition, comprising green tea leaf extract comprising from about 25–70% by weight of said composition, rhubarb root from about 25–80% by weight of said composition, and Konjac from about 5–75% by weight of said composition. Examples include, where the green tea extract is present in about 30%, the rhubarb root 5:1 extract in about 40%, and Konjac powder extract containing 90% Glucomannan in 30%; where the green tea extract is present in about 40%, the rhubarb 5:1 extract in about 45% and the Konjac powder extract containing 90% Glucomannan in 15%. Any effective amount of the composition can be administered. For instance, about 0.5 gram–20 gms, 0.5–5 gms, 0.5–3 gms, 2 gms, can be administered one or more times a day, such as three times a day, depending upon the subject's physical condition and the potency of the ingredients included. (2) The composition of (1) can further comprise sea weed from 3–50%. Examples include, where the green tea extract is present in about 30%, the rhubarb root 5:1 extract in about 40%, Konjac extract containing 90% glucomannan in about 20%, and sea weed powder in about 10%.

(3) The composition of (1) can further comprise sparganium from about 5–30% and ginseng root from about 3–15%. Examples include, where the green tea extract is present in about 25%, the rhubarb root 5:1 extract in about 32%, konjac extract containing 90% glucomannan in about 20%, sea weed dry powder in about 10%, sparganium 5:1 extract in about 10%, and ginseng root powder in about 3%; where the green tea extract is present in about 20%, the rhubarb 5:1 extract in about 40%, konjac extract containing 90% glucomannan in about 20%, sea weed dry powder in about 10%; sparganium 5:1 extract in about 8%; and ginseng root powder in about 2%.

(4) The composition of (1) can further comprise rice vinegar from about 30–300 liters per 100 kilograms of said composition. Examples include, where the green tea extract is present in about 30%, rhubarb root 5:1 extract in about 40%, konjac extract containing 90% glucomannan in about 20%, sea weed dry powder in about 10%, and 50 liter rice vinegar for every 20 kilograms of the above composition.

According to formula 4 and 5:

(1) An herbal composition comprising: Rhubarb Root 5:1 extract, 30%; Hawthorn Fruit 5:1 extract, 6%; Lotus Leaf 5:1 extract, 5%; Red Rooted Sage (Salvia Root) 5:1 extract, 5%; Alisma Root 5:1 extract, 10%; Areca Catechu Fruit 5:1 extract, 5%; Duckmeat Herb 5:1 extract, 10%; Perilla Fruit 5:1 extract, 9%; Cinnamomi Stem 5:1 extract, 10%; and Bitter Orange 5:1 extract, 10%.

(2) An herbal composition comprising: Rhubarb Root 5:1 extract, 30%; Hawthorn Fruit 5:1 extract, 6%, Lotus Leaf 5:1 extract, 5%; Red Rooted Sage (Salvia Root) 5:1 extract, 5%; Alisma Root 5:1 extract, 5%; Areca Catechu Fruit 5:1 extract, 5%; Duckmeat Herb leaf 5:1 extract, 5%; Pirelli Fruit 5:1 extract, 9%; Cinnamomi Stem 5:1 extract, 10%; Bitter Orange (Citrus aurantium 5:1 extract), 10%; and green tea leaf extract 10%.

According to formula 7:

(1) An herbal composition comprising: Green tea, from about 30–70% by weight of the composition; Ginseng, from about 1–20% by weight of the composition; Konjac, from about 10–70% by weight of the composition; and Seaweed about 10–70% by weight of the composition. The green tea can be present as an extract, e.g., comprising about 25% polyphenol and/or 7% caffeine. The ginseng can be present as a root powder or extract. The Konjac and seaweed can be used as a fine powder.

Any effective species and/or variety of ginseng can be used, e.g., Panax ginseng or Korean ginseng. Any effective species and/or variety of seaweed can used, especially, sargassum or lainaria japonica aresch.

(2) An herbal composition, comprising: about 35% by weight of green tea, about 1% by weight of ginseng, about 14% by weight of Konjac, and 50% by weight of seaweed.

The amounts of the ingredients, individually or in combination, are effective in promoting weight loss, maintaining or controlling body weight, reducing blood levels of circulating chemical fuels (e.g., glucose, carbohydrates, fatty acids, and cholesterol), facilitating or promoting metabolism, treating diabetes, treating body weight disorders, etc. An "effective amount" indicates that the mass of ingredient or ingredients in the composition is useful to achieve the purpose for which it is administered. Amounts are selected based on various factors, including age, health, gender, and weight of a patient or animal to be treated, etc. Useful amounts include, about 0.5 gram–20 gms, 0.5–5 gms, 0.5–3 gms, 2 gms, 1 gm per dosage, one or more times a day, such as twice a day, or three times a day, etc., depending upon the subject's physical condition and the potency of the ingredients included.

The ingredients can be combined in "synergistic amounts." By this, it is meant that the amounts of the ingredient present in the composition (and in combination with the other ingredients) is more effective at achieving the desired purpose (e.g., promoting weight loss) than when administered alone or in another herbal composition. Synergy indicates that the ingredients cooperate with each other to achieve an enhanced or superior result than would be achieved if either were administered alone, i.e., the effect is not additive (the sum is greater than the sum of the individual parts).

The present invention relates to methods of modulating body weight in a subject, comprising, e.g., administering to a subject in need thereof a composition comprising an effective amount of any composition, ingredient, or ingredients, as mentioned above.

By the phrase "modulating body weight in a subject," it is meant that the mass of a subject is controlled, regulated, changed, altered, modified, etc. A subject can be any individual, human or non-human animal (e.g., cow, pig, sheep, goat, mice, rats, pets, such as dogs and cats, etc.) in need of weight modulation.

The compositions are especially useful for promoting weight loss. The phrase "promoting weight loss," indicates that the compositions and methods are useful to encourage, elicit, cause, produce, etc., reduction in the mass of a subject's body. The loss in mass can be from a tissue, such as fat and muscle, where stored lipids, proteins, carbohydrates, and/or liquids, such as water, are lost. The invention is not limited by how much weight loss is promoted of facilitated. For instance, it can be 0.25%, 0.5%, 1%, 5%, 7%, 10%, or more of total body weight.

The invention is not limited by how the reduction in weight loss occurs. Various mechanisms, acting alone or in combination, produce the weight loss effect. This includes, e.g., promoting metabolism, promoting utilization of chemical fuels (e.g., fats and carbohydrates), reducing blood cholesterol levels, acting as diuretic, promoting utilization of stored fuels, such as fat from adipose tissue and glycogen, To achieve weight modulation, a composition in accordance with the present invention is administered to a subject. By the term "administered," it is meant that the composition is delivered to a subject by any means or route which is effective to achieve the desired result, including, e.g., oral, parenteral, enteral, intraperitoneal, topical, transdermal (e.g., using any standard patch), ophthalmic, nasally, local, non-oral, such as aerosal, inhalation, subcutaneous, intravenous, intramuscular, buccal, sublingual, rectal, vaginal, intra-arterial, intrathecal.

Compositions can be administered at any time suitable time. For example, compositions can be administered before, after, or together with an activity to be effected, e.g., prior or after a meal, prior to exercise, prior to a sporting event, etc. Times can vary, e.g., about 6 hours, 4 hours, 2 hours, 1.5 hours, 1 hour, 30 minutes, 15 min, 10 min, 5 min, etc., to the activity which is to be effected. Additionally, the compositions can be administered concurrently with the activity. Where weight-loss and/or control is desired, compositions of the invention can be administered when nutrients from a meal or snack begin to appear in the blood, i.e., the absorptive state, when ingested nutrients are entering the blood from the gastrointestinal tract. See, e.g., *Human Physiology*, Vander et al., Fifth Edition, 1990, e.g., Chapters 16 and 17. The adsorptive state can vary, depending upon the content of the food, e.g., from about 1 hour to about 4 hours.

The compositions can be in any effective form, including, oral, pill, capsule, troche, liquid, extract, beverage, food, tea, topical, injectable, etc. They can be administered alone, or in combination with other active or inert agent(s).

Any effective part of an herb in accordance with the present invention can be used, including to seeds, leaves, stems, flowers, roots, berries, bark, or any other plant parts that are useful for the purposes described. Herbs can be in any form which is effective, including, but not limited to dry powders, grounds, emulsions, extracts, and other conventional compositions. To extract or concentrate the effective ingredients of an herb, typically the plant part is contacted with a suitable solvent, such as water, alcohol, methanol, or any other solvents, or mixed solvents. The choice of the solvent can be made routinely, e.g., based on the properties of the active ingredient that is to be extracted or concentrated by the solvent.

Herbs can be used as 5:1 extract, e.g., an aqueous extract. This indicates that the dry weight of the herb is concentrated five times (5:1) in the extract. Any of the aforementioned formula can be prepared with a 5:1 extract, and any of the aforementioned values can refer to the weight of the extract. Green tea (O. ktze.) can be used as an extract containing about 10% caffeine and about 18% epigallocatechin) or 5:1 extract prepared from a dry powder. It can also be used as an extract containing about 7% caffeine and about 25% polyphenol.

Compositions can further comprise inert and carrier ingredients, stabilizers, antioxidants, etc., including, but not limited to, water, salt solutions, alcohols, gum arabic, vegetable oils, benzyl alcohols, gelatin, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose and the like. Other additives include, e.g., antioxidants and preservatives, coloring, flavoring and diluting agents, emulsifying and suspending agents, such as acacia, agar, alginic acid, sodium alginate, bentonite, carbomer, carrageenan, carboxymethylcellulose, cellulose, cholesterol, gelatin, hydroxyethyl cellulose, hydroxppropyl cellulose, hydroxypropyl methylcellulose, methylcellulose, octoxynol 9, oleyl alcohol, povidone, propylene glycol monostearate, sodium lauryl sulfate, sorbitan esters, stearyl alcohol, tragacanth, xanthan gum, and derivatives thereof, solvents, and miscellaneous ingredients such as microcrystalline cellulose, citric acid, dextrin, dextrose, liquid glucose, lactic acid, lactose, magnesium chloride, potassium metaphosphate, starch, and the like.

EXAMPLE

A clinical trial was performed using Tea Light, an herbal composition comprising, by weight, 35% green tea, 50% seaweed, 14% konjac, and 1% panex ginseng. A double blind, placebo controlled human clinical trial on the weight loss effect of Tea Light on a total 43 obesity patients was conducted. Patients in the Tea Light group took two Tea Light capsules (500 mg/capsule) each time, twice a day (i.e., about 2 grams/day), for six weeks. Patients in the control group took two placebo capsules (500 mg/capsule) each time, twice a day, for six weeks. Patients were instructed to avoid a diet rich in fat, sugar, and salt for the period of the treatment.

At the end of the six week trial, the average weight loss of the patients in the Tea Light group was about 5.6 kg or 12.3 lb. For the experimental group, total body weight was from about 84.2±26.5 kg before the trial, to 78.6±16 kg after taking Tea Light. For the control group, the average weight loss of the patients in the control group taking placebo capsules was about 1.9 kg or 4.2 lb. Total body weight was about from 83.8±27.6 kg before the trial, to 81.9±29.5 kg after taking the placebos. Conclusion: Tea Light was effective for promoting weight loss. The average weight loss was about 0.93 kg or 2.1 lb per week.

I claim:

1. An herbal composition comprising: green tea, ginseng, 25–500 mg of konjac extract comprising 90% glucomannan, and seaweed, wherein each ingredient is present in an amount effective to promote body weight loss, or maintain or control body weight.

2. An herbal composition of claim 1, comprising by weight, 30–70% green tea, 1–20% ginseng, 10–70% konjac extract, and 10–70% seaweed.

3. An herbal composition of claim 2, comprising by weight, 30–40% green tea, 1–5% ginseng, 10–20% konjac extract, and 40–60% seaweed.

4. An herbal composition of claim 3, comprising by weight, 35% green tea, 1% ginseng, 14% konjac extract, and 50% seaweed.

5. An herbal composition of claim 4, wherein the ginseng is panex ginseng.

6. A method of promoting weight loss, comprising administering an effective amount to a patient in need thereof of a composition of claim 4.

7. A method of claim 6, wherein 1–3 grams a day of said composition is administered.

8. A method of promoting weight loss, comprising administering an effective amount to a patient in need thereof of a composition of claim 3.

9. An herbal composition of claim 2, wherein the green tea is an extract comprising 25% polyphenol and 7% caffeine.

10. A method of promoting weight loss, comprising administering an effective amount to a patient in need thereof of a composition of claim 2.

11. An herbal composition of claim 1, wherein said amounts are effective to promote body weight loss.

12. A method of promoting weight loss, comprising administering an effective amount to a patient in need thereof of a composition of claim 1.

13. An herbal composition of claim 1, comprising 50–500 mg of konjac extract.

14. An herbal composition, comprising by weight: 30–70% green tea, 1–20% ginseng, 10–70% konjac extract comprising 90% glucomanna, and 10–70% seaweed, in amounts effective to promote body weight loss, or, maintain or control body weight.

15. A method of promoting weight loss, comprising administering an effective amount to a patient in need thereof of a composition of claim 14.

16. An herbal composition of claim 14, wherein said composition comprises 50–500 mg of konjac extract.

* * * * *